| United States Patent [19] | [11] Patent Number: 4,650,615 |
|---|---|
| Rizkalla | [45] Date of Patent: Mar. 17, 1987 |

[54] PURIFICATION OF CARBOXYLIC ACID ANHYDRIDES CONTAMINATED WITH HALOGEN OR HALIDES

[75] Inventor: Nabil Rizkalla, River Vale, N.J.

[73] Assignee: The Halcon SD Group, Inc., Little Ferry, N.J.

[21] Appl. No.: 758,633

[22] Filed: Jul. 24, 1985

[51] Int. Cl.$^4$ ............................................. C07C 51/42
[52] U.S. Cl. ..................................... 260/546; 260/549
[58] Field of Search .................. 260/546, 549, 544 A

[56] References Cited

U.S. PATENT DOCUMENTS 4,246,195 1/1981 Szecsi .................................. 260/549

FOREIGN PATENT DOCUMENTS 0135085 3/1985 European Pat. Off. .
3329781 2/1985 Fed. Rep. of Germany .

Primary Examiner—Natalie Trousof
Assistant Examiner—L. Hendriksen
Attorney, Agent, or Firm—Harold N. Wells

[57] ABSTRACT

Carboxylic acid anhydrides are freed from small amounts of halogen and halide moieties by treatment with a phenyl or an alkyl phosphine.

2 Claims, No Drawings

PURIFICATION OF CARBOXYLIC ACID ANHYDRIDES CONTAMINATED WITH HALOGEN OR HALIDES

This invention relates to the purification of carbonylation products and is more particularly concerned with the purification of carboxylic acid anhydrides, especially acetic anhydride.

Processes have been developed for the preparation of carboxylic acid anhydrides by the reaction of olefins, esters, and ethers with carbon monoxide in the presence of a catalyst system which comprises a metal catalyst component and an iodide component, generally an alkyl iodide, especially methyl iodide. Processes of this character involving a Group VIII noble metal catalyst, such as rhodium, palladium, iridium and the like are disclosed, for example, in U.S. Pat. Nos. 3,852,346, 4,115,444, 4,335,059, and 4,358,411, and in British Pat. Nos. 1,468,940 and 1,523,346. Catalyst systems of the character indicated wherein the metal component comprises nickel or nickel compounds are employed for the preparation of carboxylic anhydrides in processes which are disclosed, for example, in U.S. Pat. Nos. 4,026,677 and 4,026,678. Processes have also been disclosed wherein carboxylic anhydrides are co-produced with carboxylic acids in carbonylation systems involving Group VIII noble metal catalysts and an iodide promoter. In European patent application Nos. 0 087 869 and 0 087 870, for example, there are described processes involving the carbonylation of carboxylic acid esters, such as methyl acetate, hydrocarbyl ethers, such as dimethyl ether, and optionally also an alcohol, together with controlled, limited amounts of water. Similarly, U.S. Pat. No. 4,046,807 shows the preparation of acetic anhydride by the carbonylation of methyl acetate with a Group VIII noble metal catalyst and an iodide, wherein methanol is mixed with the methyl acetate feedstock and is converted to acetic acid so that acetic anhydride and acetic acid are co-produced in the same reaction zone. Carbonylation processes for the preparation of carboxylic acid anhydrides have also been disclosed in which the carbonylation of carboxylic acid esters and/or hydrocarbyl ethers is carried out with various catalysts, such as catalysts based on metals of Group VIII of the Periodic Table, in the presence of an iodide and in the presence of substantial quantities of carboxylic acids, especially acetic acid. Processes of this nature are disclosed, for example, in U.S. Pat. Nos. 4,115,444, 4,333,884, and 4,333,885. In the reductive carbonylation of methyl acetate or dimethyl ether to produce ethylidene diacetate as described, for example, in British Pat. No. 1,538,782, quantities of acetic anhydride are co-produced. The effluents from the processes such as referred to above are treated, usually by distillation, to separate the relatively non-volatile metal-containing catalyst component, and the liquid effluent is then separated, as by fractional distillation, into its several components including the carboxylic acid anhydride present. Whereas the major portion of the halogen or halide moiety in the effluent can be separated by such distillation and recycled to the carbonylation zone to provide the halogen or halide moiety required in the production of further quantities of carbonylation products of the character referred to above, even with relatively efficient distillation, however, the carboxylic acid anhydride recovered inevitably contains a small amount of halogen or a halogen compound, such as methyl iodide.

While the amount of the halogen or halide moiety remaining with the carboxylic acid anhydride is generally very small, yet the carboxylic acid anhydride is contaminated to an extent that is undesirable in many cases and frequently interferes with its utilization. Attempts to eliminate or reduce the quantity of the halogen or halide contaminant to acceptable levels by fractional distillation have presented problems. One of the problems encountered results from the fact that carbonylation products contain species of halogen contaminants that are highly resistant to separation by distillation. U.S. Pat. No. 4,246,195 provides a process for removing iodine moieties, especially organic iodine compounds, from carbonylation products by treating the iodine-contaminated products with cesium acetate, potassium acetate, or sodium acetate. The removal of iodine contaminants from carboxylic acids has been proposed in various patents. Thus, U.S. Pat. No. 3,772,156 purifies acetic acid to remove iodine by multiple distillation combined with treatment with one or more chemical agents. U.S. Pat. No. 3,709,795 treats the carboxylic acid with an inorganic oxidizing compound and then subjecting the treated carboxylic acid to distillation. U.S. application of H. M. Sachs and M. Becker Ser. No. 335,918 suggests the removal of iodine contaminants from acetic acid and acetic anhydride by use of an anion exchange resin. While these several processes are effective to various degrees, it is desirable to provide a less complicated method of treatment which, at the same time, is capable of reducing the halogen or halide contaminant to very low levels.

It is accordingly an object of this invention to provide an improved process for the removal of halogen or halide contaminants from carboxylic acid anhydrides recovered from carbonylation and like reaction mixtures which is effective to reduce such contaminants to low levels.

In accordance with the invention, it has been surprisingly discovered that, when the reaction component to be purified is treated in the presence of a phosphine reagent under moderate temperature and pressure conditions and for a relatively short time, the halide or halogen moieties present as contaminants in the carboxylic acid anhydride and normally resistant to separation by distillation can be substantially completely removed to leave a product which is essentially free from the halide or halogen moieties, i.e., they remain in concentrations of only a few parts per billion (ppb) and in a wholly-acceptable form for commercial use.

Thus, in accordance with the process of this invention, a liquid or vaporous body of the carboxylic acid anhydride to be purified, and which is contaminated with a small amount of halide or halogen moieties, is intimately contacted with a phosphine reagent while a gaseous stream which may comprise hydrogen may flow into the carboxylic acid anhydride being treated. It has been surprisingly discovered that such treatment effectively removes the halogen or halide moieties from the carboxylic acid anhydride-containing liquid body with the result that, when the liquid stream leaves the contact zone containing the catalyst, it is essentially free of halogen or halide moieties of any kind and is of a high purity with respect to its content of halogen values.

The carbonylation reaction component fed to the process of this invention consists essentially of a carboxylic acid anhydride, or a mixture of carboxylic acid anhydrides, e.g., acetic anhydride, propionic anhydride, n-butyric anhydride, hexanoic anhydride and other carboxylic acid anhydrides containing up to 8 carbon atoms, and contains halogen or halide impurities corresponding to or derived from the halogen or halide moieties present in the reaction zone wherein the carboxylic acid is present in the carbonylation reaction mixture produced by the carbonylation of alcohols, olefins, esters or ethers in the presence of a Group VIII metal-containing catalyst and a halogen moiety, such as described in the above-mentioned U.S. Pat. Nos. 3,852,346, 4,026,678, 4,115,444, 4,335,059 and 4,358,411, and British Pat. Nos. 1,468,940 and 1,523,346. The disclosures of said U.S. and British patents are incorporated herein by reference. The process of this invention is carried out in a substantially water-free system. The carboxylic acid stream to be treated will ordinarily be essentially free of other components in addition to the halogen or halide contaminants, but the stream may contain carbonylation-derived components such as carboxylic acids, esters, ethers, ethylidene diacetate, alcohols, and the like. Ordinarily, it is preferred that the total of such other components not exceed about 25 wt. % of the carboxylic acid anhydride stream.

The halogen and halide impurity content of the carboxylic acid anhydride feed to the process of the invention can vary, the limiting factor on the impurity level in the feed being essentially an economic one. Extensive removal of impurities from the feed by distillation prior to application of the process of this invention is generally uneconomic and, practically speaking, has not been found to be feasible. However, the greater the content of halogen and halide impurity in the feed to the process of this invention, the more extensive the treatment required. In each case, therefore, the impurity level in the feed involves an economic balance between cost of prior distillation and use of the treatment of this invention. Such considerations normally dictate feeds containing under 1,000 ppm of halogen and halide impurities, generally less than 500 ppm, and usually at most 300 ppm, all amounts referring to contained halogen, based on total feed. At least 0.001 ppm is ordinarily present.

The reagents used in the process of the invention are soluble in the body of carboxylic acid anhydride being treated and are thus homogeneous reagents as distinguished from insoluble or heterogeneous reagents. The reagents include the phenyl and alkyl phosphines such as triphenyl phosphine, tritolyl phosphine, triethyl phosphine, and tributyl phosphine. In general, each hydrocarbyl group has 1 to 10 carbon atoms and may be unsubstituted or substituted by non-reactive substituents.

A stream of hydrogen can be employed in admixture carbon monoxide, i.e., 95 hydrogen and 5 carbon monoxide to 20 hydrogen and 80 carbon monoxide by volume, and may also include inert diluents such as nitrogen, methane, and noble gases, if desired. The presence of inert diluents does not affect the reaction, but their presence makes it necessary to increase the rate of gas supplied. The hydrogen should also be essentially dry, i.e., the hydrogen and any diluents should be reasonably free from water. The presence of minor amounts of water such as may be found in the commercial forms of the gases is, however, entirely acceptable.

It is known in the art to hydrogenate acetic anhydride in the liquid phase to produce ethylidene diacetate and/or acetaldehyde. Processes of this type are disclosed, for example, in Fenton, U.S. Pat. No. 3,579,566; Wakamatsu et al., U.S. Pat. No. 3,631,188; Suzuki, U.S. Pat. No. 4,221,918; European Patent Application No. 0 034 062; and British Pat. No. 2,075,508. In these processes, however, it is necessary to use Group VIII noble metals containing or combined with biphyllic ligands or to use a special solvent or to have present a strong acid, such as sulfuric acid, or to add substantial quantities of halogen moieties and, in general, for the desired results to employ elevated temperatures and pressures. In contrast, the process of the present invention, which is not directed to producing ethylidene diacetate or acetaldehyde from the anhydride being treated but to remove contaminating halogen values, biphyllic ligands are not employed nor are strong acids nor are solvents, and clearly there is no addition of halogen values. A new and unexpected result is accordingly obtained.

Contacting of the carboxylic acid anhydride stream with the reagent can be effected in any convenient manner. For example, contacting may be effected in a stirred vessel wherein the reagent is mixed with the liquid body with good agitation while a gaseous stream may be bubbled through the liquid body and the liquid is then suitably recovered by distillation and the like. As a result of the contact in the presence of the reagent, the halogen and halide values in the stream fed to the reaction zone, and which are resistant to removal by distillation, are readily removed, and there is recovered a liquid carboxylic acid anhydride stream essentially free of halogen and halide values. The treatment of the invention can be carried out as a batch, semicontinuous or continuous operation, either with manual or automatic control, using methods and techniques well known in the art. Gas would be 5-25 mols/hour/mol of halogen.

When the treatment with the reagent has been carried out by contacting in a stirred vessel containing the reagent in the carboxylic acid anhydride stream, it will, of course, be necessary to distil or otherwise handle the treated stream to remove the reagent for reuse. The treated product may be subjected to a final distillation to recover the desired product in as pure a form as possible. No subsequent distillation may be needed, although a final distillation can be applied if desired to remove any non-halogen-containing contaminants, if present. Such distillations are, of course, known to persons skilled in the art and are not features of the present invention.

The temperatures of any gaseous stream and of the carboxylic acid anhydride being treated are selected to keep the acid anhydride in the liquid phase as it is contacted with the catalyst in the reactor at the total pressure and total gas flow rates employed. Ordinarily, the temperature will lie within the range of 20° and 200° C. Higher temperatures can be employed, but there is no particular advantage in their use.

As mentioned, it is a surprising feature of the invention that the liquid leaving the reactor is essentially free of detectable halogen values.

The reaction is carried out in a vacuum or under atmospheric or superatmospheric pressure, but excessively high pressures, which require special high-pressure equipment, are not necessary. In general, the reaction is effectively carried out by employing a pressure which is preferably 50 mmHg to 1,000 psig, although a pressure within a broader range can also be employed. Typically, from about atmospheric up to about 50 psig are used. The reaction can be advantageously carried out in a conventional autoclave.

One of the advantageous features of the invention, as applied to a halogen or halide contaminated carboxylic acid anhydride stream derived from a reaction involving carbon monoxide and or hydrogen in the presence of a halogen moiety, is that, when the gaseous non-carboxylic acid anhydride effluent of the purification of this invention contains carbon monoxide, it can be fed to the reaction from which the carboxylic acid anhydride is derived to provide some or all of the gaseous feed to that reaction.

The following example will serve to provide a fuller understanding of the invention, but it is to be understood that it is given for illustrative purposes only and is not to be construed as limitative of the invention. In the example, which is carried out at atmospheric pressure, all parts and percentages are on a weight basis unless otherwise indicated, and the "parts" or "part" mean grams or gram. In the example, "ppm" stands for parts per million, and "ppb" stands for parts per billion, and analyses were carried out by high pressure liquid chromatography, neutron activation, and polaragraphic analysis.

EXAMPLE 1

A reaction vessel provided with a refluxing condenser and a magnetic stirrer is charged with 100 parts acetic anhydride containing 808 ppb iodine and 1 part triphenyl phosphine. The mixture is stirred for two hours at refluxing temperature. Analysis of the recovered liquid reaction product indicates the presence of no free iodine or iodine-containing compounds.

I claim:

1. A process for the purification of carboxylic acid anhydrides contaminated with halogen and halide values to reduce the quantity of said values in the anhydrides, which comprises treating said anhydrides with a phenyl or an alkyl phosphine in the absence of copper, zinc, silver, and cadmium or their compounds and distilling to recover said anhydrides.

2. A process as defined in claim 1, wherein the carboxylic acid anhydride contains at least 0.001, but at most 1,000, ppm of iodine values expressed as I.

* * * * *